(12) United States Patent
Delgado

(10) Patent No.: US 9,335,279 B2
(45) Date of Patent: May 10, 2016

(54) PRE AND POST CLEANING OF MASK, WAFER, OPTICAL SURFACES FOR PREVENTION OF CONTAMINATION PRIOR TO AND AFTER INSPECTION

(75) Inventor: Gildardo Delgado, Livermore, CA (US)

(73) Assignee: KLA-Tencor Corporation, Milpitas, CA (US)

(*) Notice: Subject to any disclaimer, the term of this patent is extended or adjusted under 35 U.S.C. 154(b) by 980 days.

(21) Appl. No.: 13/450,724

(22) Filed: Apr. 19, 2012

(65) Prior Publication Data

US 2012/0274924 A1 Nov. 1, 2012

Related U.S. Application Data

(60) Provisional application No. 61/479,036, filed on Apr. 26, 2011.

(51) Int. Cl.
*B08B 9/00* (2006.01)
*G01N 21/956* (2006.01)
*B08B 7/00* (2006.01)
*G03F 1/82* (2012.01)
*G03F 1/84* (2012.01)
*G03F 7/20* (2006.01)
*G01N 21/94* (2006.01)

(52) U.S. Cl.
CPC ............ *G01N 21/956* (2013.01); *B08B 7/005* (2013.01); *B08B 7/0035* (2013.01); *B08B 7/0057* (2013.01); *G03F 1/82* (2013.01); *G03F 1/84* (2013.01); *G03F 7/70908* (2013.01); *G01N 21/94* (2013.01)

(58) Field of Classification Search
None
See application file for complete search history.

(56) References Cited

U.S. PATENT DOCUMENTS

| 6,092,714 | A | 7/2000 | Casey |
| 6,676,762 | B2 | 1/2004 | Drzal et al. |
| 6,881,687 | B1 | 4/2005 | Castrucci |
| 2006/0016458 | A1 | 1/2006 | Novak et al. |
| 2006/0225299 | A1 | 10/2006 | Kim et al. |

OTHER PUBLICATIONS

Guy P. Brasseur et al., Aeronomy of the Middle Atmosphere, Chemistry and Physics of the Stratosphere and Mesosphere, Atmospheric and Oceanographic Sciences Library, Chapter 5, pp. 272-281 Kluwer Academic Publishers Group, © 1986.
Cheng, C.C., et al., "Hydrocarbon Surface Chemistry on Si(100)", 2nd International Symposium on Atomic Layer Epitaxy Session E-12, Pittsburgh, PA, Jun. 1, 1992, 33 pages.

*Primary Examiner* — Eric Golightly
(74) *Attorney, Agent, or Firm* — Suiter Swantz pc llo

(57) ABSTRACT

A method and apparatus for preventing or minimizing contamination on a critical surface is disclosed. The method and apparatus for preventing or minimizing contamination on the critical surface may be an integrated component of an inspection system, and the cleaning process may be applied prior to the inspection process (may be referred to as pre-cleaning) which may greatly reduce photon-induced contamination. In addition, the cleaning process in accordance with the present disclosure may also be applied upon completion of the inspection process (may be referred to as post-cleaning).

6 Claims, 2 Drawing Sheets

PRE AND POST CLEANING OF MASK, WAFER, OPTICAL SURFACES FOR PREVENTION OF CONTAMINATION PRIOR TO AND AFTER INSPECTION

CROSS-REFERENCE TO RELATED APPLICATIONS

The present application claims the benefit under 35 U.S.C. §119(e) of U.S. Provisional Application Ser. No. 61/479,036, filed Apr. 26, 2011. Said U.S. Provisional Application Ser. No. 61/479,036 is hereby incorporated by reference in its entirety.

TECHNICAL FIELD

The disclosure generally relates to the field of mask and wafer inspection, and particularly to preventing or minimizing contamination during inspection.

BACKGROUND

Mask inspection, or critical optical component (e.g., reticle, wafer or the like) inspection, is an operation of checking the correctness of the fabricated masks or critical optical components. Certain inspection systems may utilize wavelengths 350 nm or below, or broadband deep ultraviolet (DUV) in the range of 180-450 nm wavelength, or wavelengths either narrow or broadband below 200 nm down to 1 nm (e.g., including EUV (13.5 nm), e-beam systems or the like).

The high-energy photons utilized by such inspection systems may interact with contaminating compounds or by the photon-induced dissociation of adsorbed hydrocarbons on the critical surfaces. Photon-induced contamination on the surfaces may arise from organic, inorganic compounds (including acids and bases) or metal compounds. This may result in undesirable growth of thin contamination films on optical elements or critical surfaces or critical components being inspected. That is, the critical surfaces being inspected may be contaminated during the inspection process.

In the absence of radiation, mask or wafer can become contaminated. Contamination may come from packaging, storage, ambient, handling, transport and from the loading process. The buildup of contamination on a mask, wafer or an optical element substrate is typically on the order of a few monolayers. Contamination growth and contamination rates depend largely on the initial amount of contaminates that exist on the mask or optical element that will be inspected. With some contamination present on the surface, photon-induced contamination easily follows when optical element is exposed to ionizing radiation. Experimental data indicates that a very modest increase of the mirror temperature can dramatically decrease the equilibrium concentration of an adsorbate and, thus, decrease the rate of carbon growth. In many cases, films from photon-induce processes cannot be easily removed and may require specific wavelength and radiation to remove. In addition, photon-induced damage of the mask or wafer may occur after the contamination deposition of a few atomic layers.

Therein lies a need for a method and apparatus for preventing or minimizing contamination on a critical surface.

SUMMARY

The present disclosure is directed to an inspection specimen cleaning system. The system may include a light source configured for providing photons towards a surface of the inspection specimen. The system may also include a gas source configured for providing a mixture of gases towards the surface of the inspection specimen. The photons in combination with the mixture of gases may form reactive free radicals to dissociate contaminate compounds on the surface of the inspection specimen.

A further embodiment of the present disclosure is also directed to a method for reducing contamination on a surface of an inspection specimen. The method may include providing photons towards the surface of the inspection specimen prior to an inspection process; and providing a mixture of gases towards the surface of the inspection specimen prior to the inspection process, wherein the photons in combination with the mixture of gases form reactive free radicals to dissociate contaminate compounds on the surface of the inspection specimen.

An additional embodiment of the present disclosure is also directed to a method for inspecting an inspection specimen. The inspection method may include pre-cleaning a surface of the inspection specimen prior to inspecting the inspection specimen. The pre-cleaning process may include providing photons towards the surface of the inspection specimen; and providing a mixture of gases towards the surface of the inspection specimen, wherein the photons in combination with the mixture of gases form reactive free radicals to dissociate contaminate compounds on the surface of the inspection specimen. The inspection method may also include inspecting the inspection specimen upon completion of said pre-cleaning the surface of the inspection specimen.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

The present disclosure is directed to a method and apparatus for preventing or minimizing contamination on a critical surface. It is contemplated that the apparatus for preventing or minimizing contamination on the critical surface may be an integrated component of an inspection system, and the cleaning process may be applied prior to the inspection process (may be referred to as pre-cleaning) which may greatly reduce photon-induced contamination. In addition, it is contemplated that the cleaning process in accordance with the present disclosure may also be applied after the inspection process (may be referred to as post-cleaning).

Figure 1:
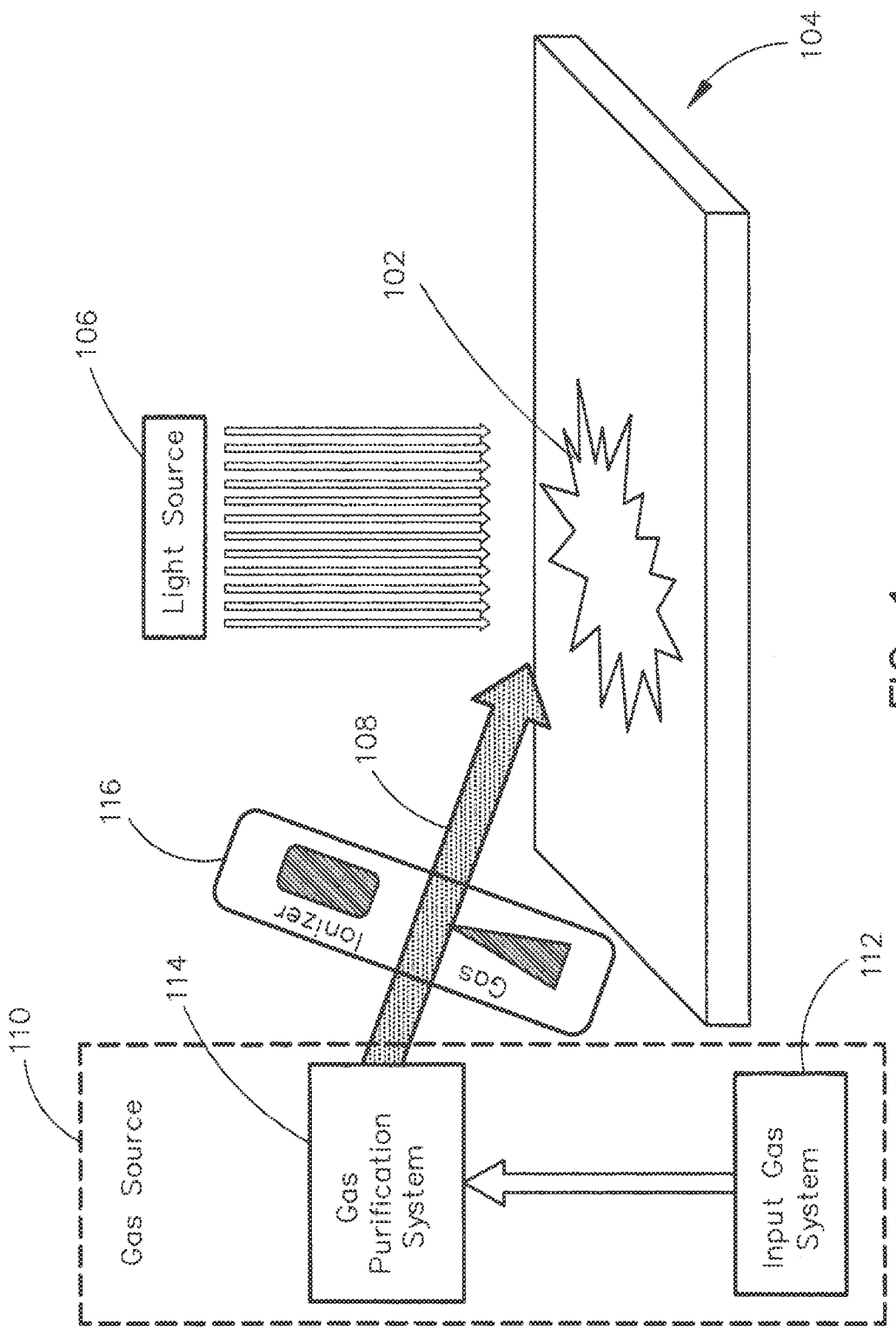
FIG. 1 is an illustration depicting a system for preventing or minimizing contamination on a surface of an inspection specimen.

Referring to FIG. 1, an illustration depicting a cleaning system 100 in accordance with the present disclosure is shown. As depicted in the figure, contaminate compounds 102 may reside on the surface of the inspection specimen 104. The term inspection specimen used in the present disclosure may include wafers, masks, reticle, solar cell, optical components and various other types of polished plates and the like. An objective of the cleaning system 100 therefore is to clean the contaminate compounds 102 on the surface of the inspection specimen 104 prior to the inspection process. Such a pre-cleaning process may prevent or minimize contamination to the inspection specimen 104 due to inspection with e-beam systems, UV laser lights, lamps, plasma sources including laser produced plasmas and the like.

In one embodiment, the cleaning system 100 may utilize a light source 106 configured for providing photon energy at or slightly higher than the binding energies of contaminants. Furthermore, the photon energy provided by the light source 106 may be utilized in combination with a mixture of gas 108 to dissociate the contaminants 102.

For instance, the light source 106 may provide extreme ultraviolet (EUV), vacuum ultraviolet (VUV), deep ultraviolet (DUV), ultraviolet (UV), visible light, infrared (IR) or the like to the surface of the inspection specimen 104. EUV, VUV or DUV photons in combination with $H_2$, $N_2$, He, Ar, Xe, $H_2O$, $O_2$, $O_3$, $CO_2$ or other gases may form reactive free radicals to dissociate the contaminate compounds 102. If the contaminate compounds 102 include multiple contaminated species, using mixtures of gasses may help targeting different contaminated species that need to be cleaned. One may target specific contaminants by selecting the correct gas (or the combination of gases) to induce the photodissociation. In addition, multiple wavelengths or combinations of EUV, VUV, DUV, UV, Visible, IR or the like may be utilized to create target free radicals from single gas or mixture of gasses. In this manner, various types of photons provided by the light source 106 in combination with various types of gasses may effectively deliver free radicals that may react with the contaminate compounds 102 and therefore clean the surface of the inspection specimen 104.

For example, introducing $O_3$ and exposing the gas to visible wavelength may provide very high cleaning efficiency for carbon; purified $O_2$ with 2-20 ppm $H_2O$ may be useful for cleaning carbon contamination for wavelength 355 and 266 nm; and the mixtures of 1000 ppm $O_2$ with 2 ppm $H_2O$ works well for carbon contamination for wavelengths at 193 nm. However, it is understood that such gas mixtures are merely exemplary. Various other mixtures and/or exposure to light sources may be utilized without departing from the spirit and scope of the present disclosure.

In one embodiment, a gas source 110 is utilized for providing the mixture of inner gases or ionized gases towards for the cleaning process. The gas source 110 may include a gas input module 112 (e.g., a concentrator, a generator, a storage device or the like) configured for providing the gas needed to a gas purification module 114. The gas purification module 114 may utilize any conventional gas purification techniques to purify and remove any contaminants that may exist in the gas provided by the gas input module 112. For instance, the gas purification module 114 may be capable of purifying organics, acids, bases, $H_2O$ as well as $O_2$ when needed. The purified gas 108 may then be directed towards the surface of the inspection specimen 104 for cleaning purposes as described above. Optionally, a gas ionizer 116 may be utilized to ionize the purified gas 108 before the gas 108 arrives at the surface of the inspection specimen 104.

In one embodiment, purified $O_2$ or clean dry air (CDA) may be utilized as the gas 108 and an Hg—Xe lamp with wavelength 185 nm, 254 and 365 nm may be utilized as the light source 106 for the cleaning process in accordance with the present disclosure. It is contemplated that the CDA may also be mixed with nitrogen and/or other types of gas as well. Furthermore, it is understood that the specific wavelengths described above are merely exemplary. Other types of light sources and gases may be utilized without departing from the spirit and scope of the present disclosure.

For instance, molecular oxygen in excited or excited metastable states may react with organic and other contaminates to clean the surface. Atomic oxygen $O(^3P)$ and $O(^1D)$ are highly reactive and may interact with organic contaminants on surfaces to form CO and $CO_2$ and thus clean the contaminated surface. $O_3$ may also react with contaminated surfaces and therefore clean the surface. In addition, $O_2$ molecules that absorb UV with energy above the BDE of 5.43 EV ($\lambda$=243 nm) may dissociate to form atomic oxygen. Since the $O_2$ dissociation energy only requires 243 nm, the region between 243 nm and 175 nm will lead to dissociation of $O_2$, as expressed in: $O_2 + h\nu_{<243} \rightarrow O(^3P) + O(^3P)$.

In other examples, absorption with wavelength below 175 nm may produce one ground state O atom and one atom of $O(^1D)$, as expressed in: $O_2 + h\nu_{<175} \rightarrow O(^3P) + O(^1D)$. Furthermore, $O_2$ gas and a Hg—Xe lamp may also be utilized for the cleaning process, as $O_2 + h\nu_{<243} \rightarrow O(^3P) + O(^3P)$ (i.e., oxygen dissociation) and $O(^3P) + O_2 \rightarrow O_3$ (i.e., ozone formation), and an UV generated ozone cleaning process may be utilized to remove the zone: 3C+2O3 CO2 (or CO).

It is contemplated that other photodissociation and photodetachment of $O_3$ may also be utilized. For instance, the O—$O_2$ bond in ozone (O3) requires only 1.1 eV for dissociation. This corresponds to a wavelength of $\lambda$=1122 nm for breaking this bond. This wavelength is in the near infrared region of the spectrum. Thus, based on simple thermochemistry, visible light would be sufficient energy to break this bond in ozone. In spite of the small binding energy ($O_2$—O) of about 1 eV, the photodissociation cross section rises steeply around and below 300 nm (4 eV photons). Visible and wavelengths below 300 nm are present in a Hg—Xe lamp. This process yields dominantly singlet molecular oxygen and excited atomic oxygen $O(^1D)$: $O_3 + h\nu_{>1.1\,eV} \rightarrow O_2 + O(^1D)$.

In addition, cleaning processes such as $CO_2$ snow cleaning and/or plasma cleaning may be utilized. $CO_2$ snow cleaning process may remove micron and submicron particulates and hydrocarbon-based contamination. The cleaning process is based upon the expansion of either liquid or gaseous carbon dioxide through an orifice. This expansion leads to the nucleation of small dry ice particles and a high velocity gas carrier stream. Upon impact with a contaminated surface, the dry ice media removes particles by momentum transfer, even micron and submicron particulates, and hydrocarbons via a transient solvent or a freeze fracture mechanism. The high-velocity gas blows the contaminants into desired direction. $CO_2$ snow cleaning may therefore be utilized for either initial or final cleaning, and for numerous critical and noncritical cleaning applications. Plasma cleaning such as $H_2$ or He plasma cleaning may also be utilized, wherein the $H_2$ or He may be generated by a hot tungsten filament, RF generation, DC or AC electrical discharge source.

Figure 2:
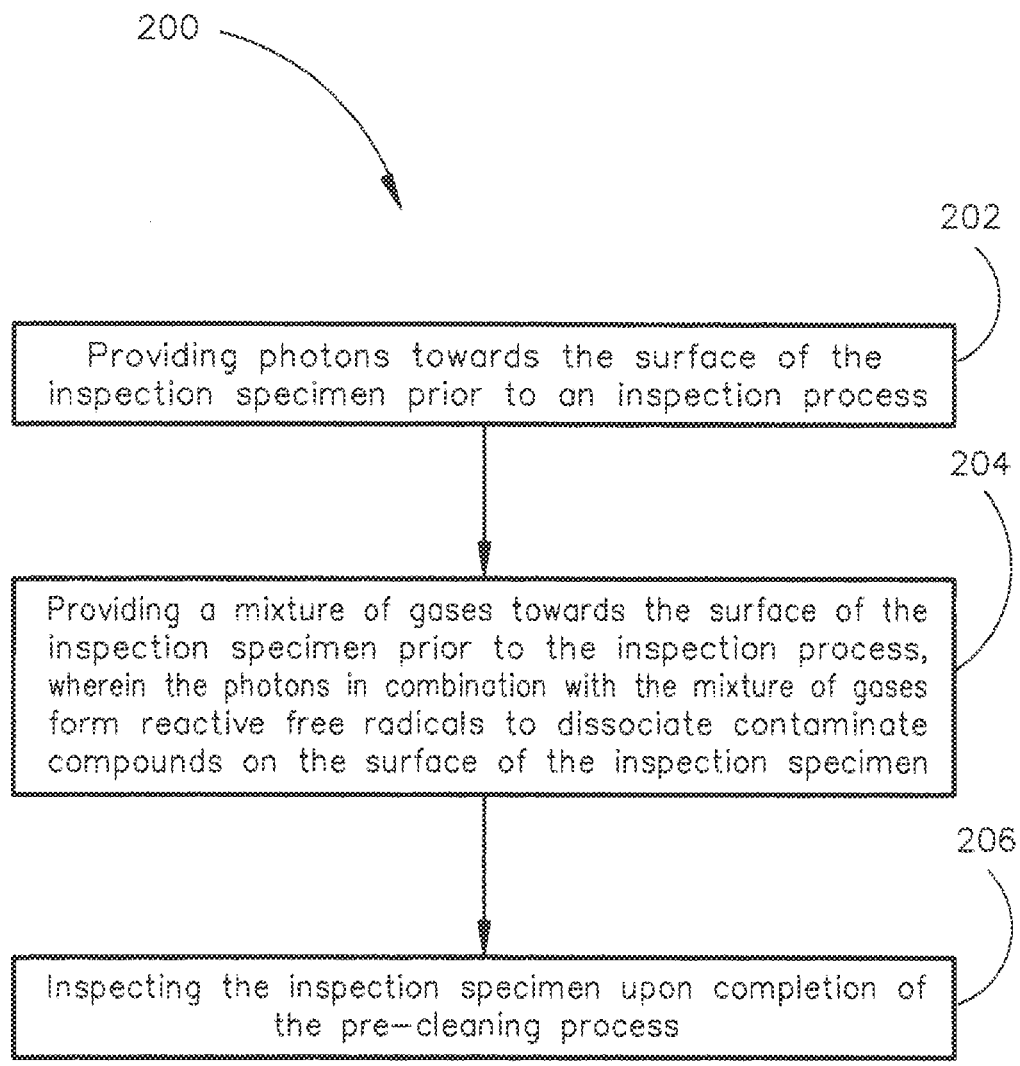
FIG. 2 is a flow diagram illustrating a method for reducing contamination on a surface of an inspection specimen in accordance with the present disclosure.

FIG. 2 shows a flow diagram illustrating steps performed by a method 200 for cleaning the surface of the inspection specimen. Step 202 may provide a light source directly facing the surface of the inspection specimen to be cleaned. Step 204 may deliver a mixture of gas towards the surface of the inspection specimen. The photons provided by the light source in combination with the mixture of gas delivered to the surface of the inspection specimen may form reactive free radicals to dissociate the contaminants on the surface of the inspection specimen. In one embodiment, the inspection process 206 may start upon the completion of steps 202 and 204.

It is contemplated that step 204 may further include steps to purify the gas from a gas input module. In addition, the purified gas may be ionized before being delivered towards the surface of the inspection specimen.

While the examples above illustrate using the method and system in accordance with the present disclosure to clean the inspection specimen prior to the inspection process (i.e., pre-cleaning of the inspection specimen), it is contemplated that the method and system in accordance with the present disclosure may also be utilized to clean the inspection specimen upon completion of the inspection process (i.e., post-cleaning of the specimen). That is, the specific application and when to apply the method and system in accordance with the present disclosure may vary without departing from the spirit and scope of the present disclosure. Furthermore, it is contemplated that the pre-cleaning and the post-cleaning process in accordance with the present disclosure may be utilized to target the same or different types of contaminated species that need to be cleaned.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. An inspection specimen cleaning system, comprising:
   a light source, the light source configured to provide a mixture of photons generated by at least one of: an extreme ultraviolet (EUV) light source, a vacuum ultraviolet (VUV) light source, a deep ultraviolet (DUV) light source, an ultraviolet (UV) light source, a visible light source or an infrared (IR) light source towards a surface of the inspection specimen; and
   a gas source, the gas source configured to provide a mixture of gases that includes at least two of: $H_2$, $N_2$, He, Ar, Xe, $H_2O$, $O_2$, $O_3$ or $CO_2$ towards the surface of the inspection specimen;
   wherein the as source is controlled through a processor that executes a set of instructions stored on a processor-readable storage medium, and wherein when the set of instructions is executed, a composition of the mixture of gases is selected to form reactive free radicals in combination with the mixture of photons to dissociate contaminate compounds on the surface of the inspection specimen.

2. The inspection specimen cleaning system of claim 1, wherein the gas source is a mixed gas supply comprising at least two of: H2, N2, He, Ar, Xe, H2O, O2, O3 or CO2 gases, and wherein the mixture of gases is selected to target a plurality of contaminated species.

3. The inspection specimen cleaning system of claim 1, wherein the gas source further comprises:
   a gas purification module, the gas purification module configured for purifying the mixture of gases prior to directing the mixture of gases towards the surface of the inspection specimen.

4. The inspection specimen cleaning system of claim 1, further comprising:
   a gas ionizer, the gas ionizer configured for ionizing the mixture of gases prior to directing the mixture of gases towards the surface of the inspection specimen.

5. The inspection specimen cleaning system of claim 1, wherein the inspection specimen cleaning system is an integrated component of an inspection system, and wherein the cleaning system is utilized prior to an inspection process.

6. The inspection specimen cleaning system of claim 1, wherein the inspection specimen cleaning system is an integrated component of an inspection system, and wherein the cleaning system is utilized prior to and upon completion of an inspection process.

* * * * *